United States Patent [19]

Lobdell

[11] 4,197,876
[45] Apr. 15, 1980

[54] FLUID VALVE

[75] Inventor: Donn D. Lobdell, Golden, Colo.

[73] Assignee: Cobe Laboratories, Inc., Lakewood, Colo.

[21] Appl. No.: 938,250

[22] Filed: Aug. 30, 1978

[51] Int. Cl.² ............... F16K 5/04; F16K 27/06
[52] U.S. Cl. ..................... 137/625.47; 251/366
[58] Field of Search ............ 137/340, 375, 625.47, 137/625.41; 251/366

[56] References Cited

U.S. PATENT DOCUMENTS

| 260,985 | 7/1882 | Hughes | 137/625.68 |
| 697,284 | 4/1902 | Skiffington | 251/366 X |
| 1,160,703 | 11/1915 | Fleming | 251/366 X |
| 3,188,724 | 6/1965 | Bates et al. | 251/366 X |
| 3,481,367 | 12/1969 | Deuschle | 137/625.47 |
| 3,490,736 | 1/1970 | Snyder | 137/375 X |
| 3,935,108 | 1/1976 | Forgues | 137/625.47 X |

*Primary Examiner*—Arnold Rosenthal

[57] ABSTRACT

A fluid valve with a core received in the bore of a valve body, the bore being positioned in a separate inner body spaced radially inward from and connected by support means to the main valve body so as to hasten cooling of the bore during manufacturing and thereby improve sealing of the core by reducing dimensional variations in the bore.

11 Claims, 3 Drawing Figures

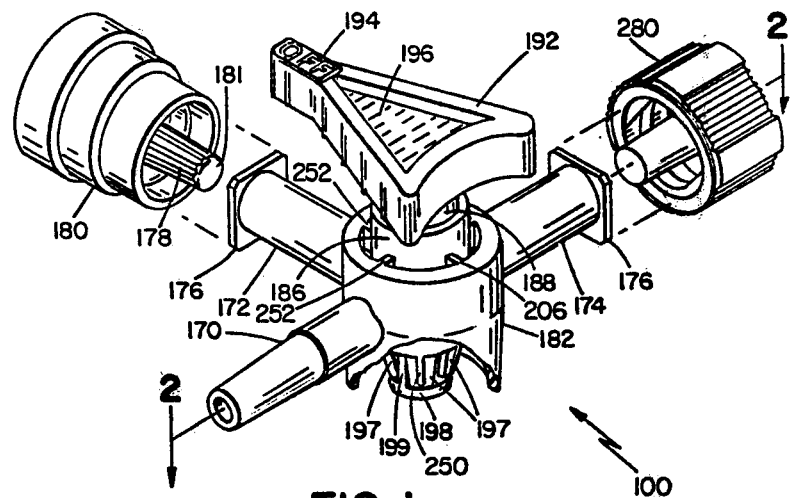
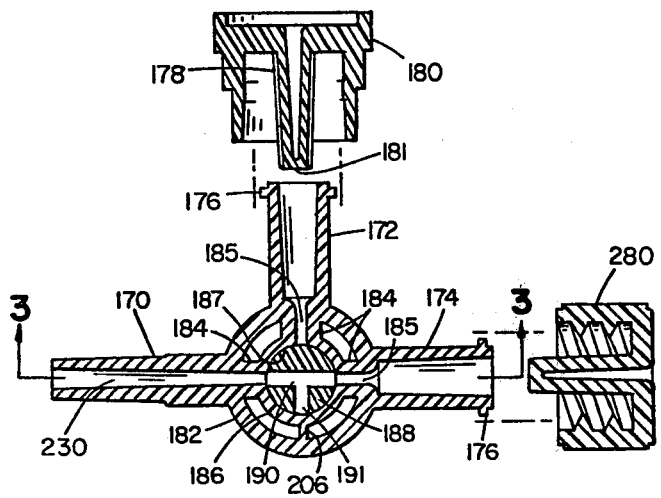
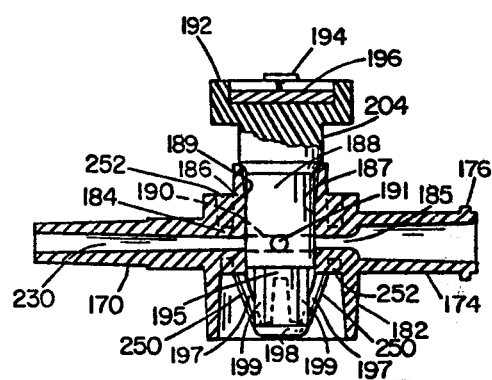

FLUID VALVE

FIELD OF THE INVENTION

This invention relates to fluid valves, particularly to stopcock valves wherein fluid flow is shut off by a 90 degree turn of a valve handle.

BACKGROUND OF THE INVENTION

Stopcocks have long been used to meter fluids. A core with an internal passage is received in the bore of a valve body, and rotation of the core by means of an attached handle brings the internal passage into or out of communication with fluid passages in the valve body. A close fit must be achieved between the bore and core so as to minimize leakage while allowing for unimpeded core rotation. In stopcocks assembled from molded thermoplastic parts, distortions in the shape of the bore introduced during cooling contribute to sealing deficiencies unless compensated for by increased fit interference between the core and bore. Greater interference, however, leads to undesirably high turning torque for the core. The distortions are the result of nonuniform rates of cooling of different portions of the valve body. External fittings generally solidify first, and the natural shrinkage occurring on cooling tends to draw still-molten material away from the valve body, thereby leaving sinks or depressions in the bore opposite the fittings.

A stopcock manufactured by Pharmaseal, Inc., Glendale, Calif., comprises a molded tubular valve body and a core held together by a friction cap pressed onto one end of the core after its installation through the valve body. Integral fittings are secured to the exterior of the tubular body, and the core and tubular interior of the valve body are both slightly tapered to allow the slightly larger core to achieve an interference fit with the body when the two pieces are axially forced together.

SUMMARY OF THE INVENTION

I have discovered that a seal between the core and valve body of a stopcock that is highly resistant to leakage can be achieved with less interference between the core and the body and thus reduced turning torque by dividing the valve body into an inner body in which the core is received and an outer body to which fittings are secured. The inner body is positioned in a hollow portion of and spaced radially inward from the outer body, and supporting spokes and fluid conduits connect the two bodies. A further advantage of this configuration is that the outer body can be extended sufficiently below the inner body and lower end of the core to allow the stopcock to rest on or be secured to a flat panel.

In preferred embodiments, the spokes and fluid conduits are made smaller in cross-sectional size than the external fittings to reduce the size of depressions the spokes and conduits could cause by cooling sooner than the inner body, the location of the spokes and conduits between the inner and outer bodies allowing them to be substantially smaller than the external fittings which are cantilevered from the body and must withstand externally-applied bending moments; the wall thickness of the outer body is made larger than that of the inner body to assure that the inner body cools first, thereby preventing depressions from forming on the inner body, depressions forming instead on the outer body, where they do not affect sealing; the core and bore are cylindrical, eliminating the taper found in some conventional stopcocks, the taper being capable of causing axial separation of the core from the body under failure of the core-to-body retention means; the inner and outer bodies comprise concentric rings; and four 90° spaced spokes extend between the bodies, three spokes including integral fluid conduits.

PREFERRED EMBODIMENT

I turn now to description of the structure and operation of a preferred embodiment of the invention, after first briefly describing the drawings.

DRAWINGS

FIG. 1 is an isometric view of the presently preferred embodiment of the invention.

FIG. 2 is a sectional view taken through 2—2 of FIG. 1.

FIG. 3 is a sectional view taken through 3—3 of FIGS. 1 and 2.

DESCRIPTION

Stopcock 100 has a male inlet tube 170 which is adapted for connection to either tubing or a female Luer lock fitting and may be adapted for connection to a reservoir. Spaced 90° and 180° from inlet tube 170 are outlet fittings 172, 174 each with female Luer lock fitting 176 and each capable of mating with vented cap 180, Luer lock cap 280, or with flexible tubing (not shown). A plurality of stopcocks can be connected together by inserting one stopcock's inlet tube 170, which is tapered, into either of fittings 172, 174 of another stopcock. Vented cap 180 has grooves 178 in central plug 181 to allow gas to escape from the outlet fitting. Inlet tube 170 and fittings 172, 174 are integral extensions of cylindrical valve body 182. Three smaller tubes 184 (FIGS. 2 and 3) connect inlet tube 170 and fittings 172, 174, respectively, with ports on bore 187 of cylindrical inner sleeve 186. Tapered inlet passage 230 extends from inlet tube 170 through its associated tube 184 to bore 187. Passages 185 connect the tapered interiors of fittings 172, 174 with bore 187. The transitions between passages 185 and the fitting interiors are rounded to smooth fluid flow through the valve. Strut portions 252 axially straddle tubes 184 to provide strength. Continuous strut 206 forms a fourth support spoke between valve body 182 and inner sleeve 186. Strut 206 is positioned directly opposite the plastic-injection region or gate (not shown) which is adjacent on the outside surface of valve body 182 and through which molten plastic is injected into the mold to form the stopcock. Strut 206 is by its location the principal conduit during molding through which molten plastic travels to reach inner sleeve 186. Valve body 182 and inner sleeve 186 and all parts integral with them are molded from transparent polycarbonate plastic. Use of transparent plastic allows detection of fluid-entrained bubbles that may be held in stopcock passages. Inner sleeve 186 surrounds cylindrical core 188 made from Delrin 500 (DuPont trademark) acetal. The core has passages 190, 191 forming a "T" cut through it for establishing fluid connections between inlet tube 170 and fittings 172, 174. Handle 192 with pointer 194 (labelled "OFF") and colored polystyrene triangular insert 196 is integral with core 188. Pointer 194 extends in a direction 180° from passage 191. Core 188 is retained in sleeve 186 by four inwardly tapered fingers 197 extending from and integral with the bottom of the sleeve and acting against annular lip 198 on the end of lower, radially-reduced cylindrical extension 195 of the core. For increased bending stiffness, each finger 197 has longitudinal ridge 250 angularly-centered on its outer surface. Assembly of the stopcock is achieved by simply pushing core 188 down into inner sleeve 186 until lip 198 snaps past fingers 197. To ease installation of core 188, the interior diameter of sleeve 186 is slightly enlarged at mouth 189. Further downward motion of core 188 is resisted by the interior surface of mouth 189, which acts as a seat for radially enlarged neck 204 of the core. Two detent ridges 199 spaced 180° apart extend radially outward from extension 195 into the grooves formed between fingers 197. Dow Corning 360 silicone fluid is used as a lubricant between core 188 and sleeve 186.

Valve body 182 has a 0.482 inch outside diameter and 0.061 inch wall thickness. Sleeve 186 has a 0.30 inch outside diameter and 0.050 inch wall thickness. Bore 187 is between 0.199 and 0.200 inch in diameter. Core 188 is between 0.202 and 0.204 in outside diameter in the axial region in contact with bore 187, for an interference fit. Fourth spoke 206 is 0.027 inch thick and is 0.23 inch long axially. Strut portions 252 are also 0.027 inch thick, and smaller tubes 184 have 0.120 inch outside diameters and 0.032 inch wall thicknesses. Inlet fitting 170 has an outside diameter of 0.180 inch at the cylindrical portion closest the valve body. Fittings 172 and 174 have 0.220 inch outside diameters. Core passages 190, 191 are 0.061 inch in diameter, just slightly larger than the 0.056 inch diameter of passages 185, 230 at bore 187.

OPERATION

To operate the stopcock, pointer 194 (FIG. 1) is rotated to whichever of the three inlet and outlet ports is to be shut off, thereby providing a fluid path along passages 190, 191 between the two remaining ports. In the figures pointer 194 is aimed at fitting 172, and passage 190 completes the fluid connection between inlet tube 170 and fitting 174. As core 188 is turned 90° between ports, detent ridges 199 outwardly deflect opposed pairs of fingers 197, and then snap into the grooves formed between the fingers upon reaching the new position, thereby providing tactile position feedback for the operator at each 90° spaced position of handle 192. To shut off both outlet fittings 172, 174 from inlet tube 170, pointer 194 is rotated to inlet fitting 170. To connect both outlet fittings to the inlet tube, the pointer is rotated to a position 180° from fitting 172.

INCORPORATION BY REFERENCE

I incorporate by reference the copending U.S. patent application of Donn D. Lobdell and Stephen J. Herman entitled "Gas Exchange Apparatus", Ser. No. 917,350, filed June 20, 1978, to illustrate one application of the invention as part of a blood oxygenator.

OTHER INVENTION

Providing radially resilient fingers on the valve body which cooperate with a lip on the core to retain the core was the invention of Joel F. Giurtino.

What is claimed is:

1. In a rotary stopcock valve including a molded plastic valve body, said body including on its outside surface integral external fittings for attachment of tubing carrying fluids to and from said valve, and a plastic valve core, said core being received in an interior bore of said valve body, said valve body including internal passages communicating between said ports on said bore, and said valve core including a plurality of passages for communicating between said ports on said bore, said core having a larger outside diameter than the internal diameter of said bore so as to provide an interference fit between said bore and core, the interference fit providing a seal to prevent leakage along said bore from said ports, the improvement wherein said molded valve body comprises an outer and an inner tubular body,
said inner and outer bodies being molded as integral portions of said molded valve body,
said inner tubular body being spaced radially inward from, and generally concentric with, said outer body, thereby forming an annular gap between said bodies, said gap being open to the ambient at at least one axial end,
said bore being centrally located in said inner body, and
said external fittings being located on the outside of said outer body,
a plurality of spokes extending generally radially across said annular gap formed between said inner and outer bodies, said spokes being molded as integral portions of said valve body,
at least one of said spokes including an inlet passage for carrying fluid entering said valve and at least one other of said spokes including an outlet passage for carrying fluid exiting from said valve.

2. The fluid valve of claim 1 wherein the wall thickness of said valve body is greater than the wall thickness of said inner body.

3. The fluid valve of claim 1 wherein said spokes are smaller in transverse cross section than said external fittings, thereby reducing the size of depressions in said bore that said spokes can cause during cooling, said transverse cross-sectional area being measured at right angles to the radial, with respect to said bodies, direction and including the fluid passage areas within said spokes and fittings.

4. The fluid valve of claim 1 wherein said spokes with integral fluid conduits each comprise two struts of rectangular transverse cross section axially straddling a tubular conduit and said other spoke or spokes each comprise a single strut of rectangular transverse cross section.

5. The fluid valve of claim 1 wherein said tubular bodies are cylindrical and concentric with said bore.

6. The fluid valve of claim 1 or 5 wherein said core and bore comprise cylindrical mating portions.

7. The fluid valve of claim 1, 2, or 3 wherein the outside diameter of said core exceeds the inside diameter of said bore at corresponding axial locations on said core and bore by between 0.002 and 0.005 inches, thereby providing sufficient interference to prevent leakage while reducing the torque required to rotate said core.

8. The fluid valve of claim 3 wherein the ratio of the total transverse cross-sectional area of all spokes to the total cross-sectional area of said external fittings is less than 0.50, said transverse cross-sectional area being measured at right angles to the radial, with respect to said bodies, direction and including the fluid passage areas within said spokes and fittings.

9. The fluid valve of claim 1 wherein there are three of said ports on said bore, said three ports are positioned 90 degrees apart, and said internal passage in said valve core connects three openings spaced 90 degrees apart, whereby in one angular orientation of said core said three openings are each aligned with one of said three ports, thereby establishing fluid communication between all said ports.

10. The fluid valve of claim 9 wherein said core further comprises a handle having a pointer, said pointer extending in a direction 180 degrees from the central opening of said three core openings, whereby said pointer on said valve core indicates the port on said bore not in fluid communication with the other said ports on said bore.

11. The fluid valve of claim 10 wherein said handle further includes a removable colored identification insert.

* * * * *